United States Patent [19]

Kiri

[11] Patent Number: 4,742,230
[45] Date of Patent: May 3, 1988

[54] X-RAY IMAGE DETECTING APPARATUS

[75] Inventor: Motosada Kiri, Kyoto, Japan

[73] Assignee: Shimadzu Corporation, Kyoto, Japan

[21] Appl. No.: 902,215

[22] Filed: Aug. 29, 1986

[30] Foreign Application Priority Data

Sep. 2, 1985 [JP] Japan .............................. 60-134818[U]

[51] Int. Cl.⁴ ............................................... G01T 1/20
[52] U.S. Cl. ................................ 250/363 S; 250/366; 250/369
[58] Field of Search ......... 250/369, 366, 367, 363 SG, 250/363 SE; 358/111; 364/414; 378/19

[56] References Cited

U.S. PATENT DOCUMENTS

| | | | |
|---|---|---|---|
| 3,515,878 | 6/1970 | Ried, Jr. et al. | 250/369 |
| 3,675,020 | 7/1972 | Siedband et al. | 250/366 |
| 4,055,767 | 10/1977 | Allemand | 378/19 |
| 4,115,694 | 9/1978 | Lange et al. | 250/369 |
| 4,142,102 | 2/1979 | Lange | 250/369 |
| 4,335,307 | 6/1982 | DeVries et al. | 358/111 |
| 4,472,728 | 9/1984 | Grant et al. | 250/367 |
| 4,472,823 | 9/1984 | Waltham | 378/19 |
| 4,611,283 | 9/1986 | Lumelsky et al. | 250/369 |

Primary Examiner—Janice A. Howell
Assistant Examiner—William F. Rauchholz
Attorney, Agent, or Firm—Koda and Androlia

[57] ABSTRACT

An X-ray image detecting apparatus having its X-ray receiving plane composed of a two-dimensional array of X-ray sensors and being devised so as to make the picturing of a detected X-ray image free from the brightness irregularity due to the sensitivity variations of the individual X-ray sensors. Each of the X-ray sensors is accompanied by a circuit means for converting the optical output of the X-ray sensor to an electric picture element signal inversely proportional to the sensitivity of the X-ray sensor, thereby enabling a detected X-ray image to be pictured without the brightness irregularity.

5 Claims, 3 Drawing Sheets

X-RAY IMAGE DETECTING APPARATUS

BACKGROUND OF THE INVENTION

The present invention relates to an X-ray image detecting apparatus, and more particularly to such an apparatus having its X-ray receiving plane composed of a two-dimensional array of X-ray sensors each of which constitutes a unit X-ray detector together with accompanying electronic elements.

Conventionally, an X-ray image is generally detected either with an X-ray camera using an X-ray film or with an apparatus devised so as to record on a tape recorder an X-ray image received by a TV camera through an X-ray image intensifier. The former method disadvantageously needs a long time to finally provide the picture of a detected X-ray image, while the latter, though more advantageous than the former in the rapidity of image detection, has an important disadvantage that the dynamic range of the X-ray image intensifier is smaller than that of a general X-ray image to be detected, resulting in the deterioration of the quality of the picture obtained from the X-ray image.

To overcome the disadvantages mentioned above, there has been provided a method in which X-ray receiving plane consists of a two-dimensional array, for example, of X-ray scintillators as X-ray sensors constituting picture elements, and the outputs from the scintillators are converted to electric signals and then recorded as a picture signal on a tape recorder. Each of the X-ray scintillators for detecting irradiated X-ray photons constitutes a unit X-ray detector together with a semiconductor photosensor for converting the optical scintillator output to corresponding electric pulse signals and a counter for counting the pulses outputted from the photosensor. Many such unit X-ray sensors are assembled in the form of a LSI (Large Scale Integrated Circuit) with their scintillator parts arranged in a two-dimensional array, on which an X-ray image is projected. However, this method necessitates some means for correcting the brightness irregularity which may appear, unless corrected, on an obtained picture owing to the sensitivily variations of the individual unit X-ray detectors, namely, of the scintillators and photosensors contained in the detectors. In a conventional typical method of correcting such brightness irregularity, a standard X-ray image with a uniform intensity throughout the entire X-ray receiving area is detected and recorded in the beginning for obtaining data of standard brightness irregularity, which data are to be used for correcting the brightness irregularity of the picture obtained from a general X-ray image to be detected. However, practising such a conventional method of correcting brightness irregularity needs a computer to perform the arithmetic operations necessary to properly display a detected image. The incorporation of a computer not only necessitates a long time to obtain a picture of the detected image because of the process of arithmetic operations for correcting the brightness irregularity, but also increases the entire cost of the apparatus.

OBJECTS AND SUMMARY OF THE INVENTION

The present invention aims at eliminating the above-mentioned disadvantages accompanying an X-ray detecting apparatus consisting of unit X-ray detectors with the X-ray image receiving plane made up of a two-dimensional array of X-ray scintillators each of which is a constituent of each of the unit detectors, and makes it an object to provide an improved X-ray image detecting apparatus that does not need a computer, though constituted with an assembly of unit X-ray detectors, for correcting the brightness irregularity caused by the sensitivity variations of the individual X-ray detectors.

Another object of the present invention is to constitute such an improved X-ray image detecting apparatus so that the brightness correction may be instantly performed to give picture signals properly representing the detected X-ray image without taking an additional time.

To achieve the above objects, though the apparatus according to the present invention also consists of an assembly of unit X-ray detectors, each of the unit X-ray detectors comprises a gate circuit and a register in addition to an X-ray scintillator, a photosensor and a pulse counter. As is mentioned later, if the X-ray scintillator as an X-ray sensor is replaced with an element capable of converting irradiated X-ray photons to electric signals directly, the photosensor is of course neglected. Many such unit X-ray detectors are assembled with their X-ray scintillator portions arranged in a two-dimensional array to form an X-ray image receiving plane. The arrangement of the scintillator portions is the same as that in the previously mentioned prior art apparatus consisting of an assembly of unit X-ray detectors each of which is not provided with a gate circuit and register.

With such a constitution of the apparatus, the X-ray image receiving plane consisting of the X-ray scintillators included as X-ray sensors in the unit X-ray detectors is first irradiated with uniform X-rays to obtain the data for correcting the picture brightness irregularity caused by the sensitivity variation of the individual X-ray scintillators and photosensors constituting the unit X-ray detectors. Irradiated with the uniform X-rays, the X-ray scintillator in each unit X-ray detector generates optical pulses. The optical output from the scintillator is converted to an electric pulse signal by the photosensor coupled to the scintillator, and the electric pulse signal is counted by the pulse counter and then stored in the register as brightness correcting data. The number of count is in accorance with the sensitivity of the scintillator and photosensor. When an X-ray image to be detected is projected on the X-ray image receiving plane, the output from the photosensor is led to the counter through an output gate circuit, which is made open only during a period inversely proportional to the above brightness correcting data stored in the register. Thus, the picture brightness variations due to the sensitivity variations of the individual unit X-ray detectors (namely of the scintillators and the photosensors), not due to the spatial brightness variations of the detected X-ray image, are corrected to give a picture regularly representing the detected X-ray image. Incidentally, the X-ray scintillator- photosensor constituting the X-ray sensor of the unit X-ray detector can be replaced with an element. capable of converting X-ray photons directly to electric signals. In this case the photosensor included in the unit X-ray detector is deleted, and the element plays a role of the combination of the X-ray scintillator and the photosensor. The details of the constitution and performance of the present invention will be described later in reference to preferred embodiments of the present invention.

DETAILED DESCRIPTION OF THE INVENTION

Figure 1:
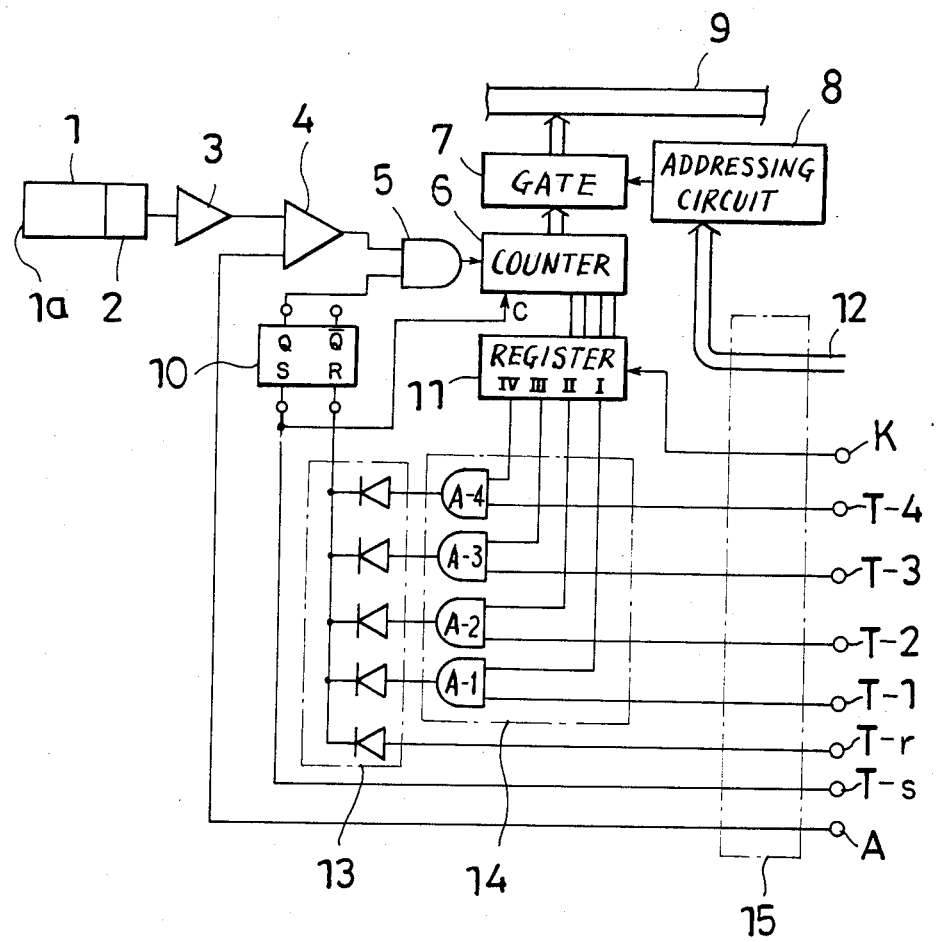
FIG. 1 shows a circuit constitution of the unit X-ray detector used in an embodiment of the present invention.
Figure 3:
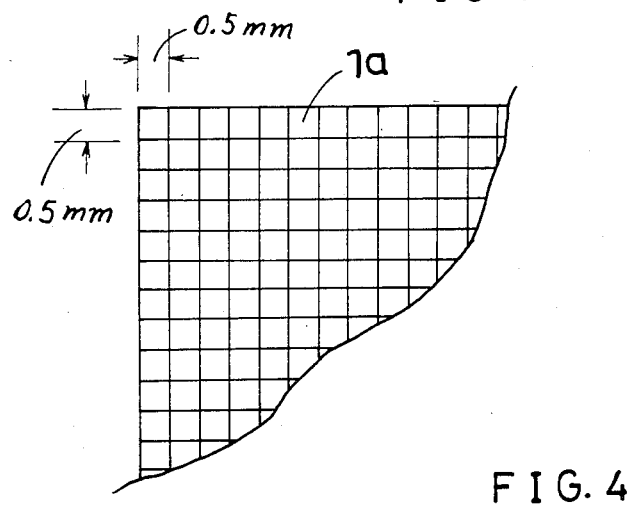
FIG. 3 shows an X-ray receiving plane of the above embodiments.

Each one of the unit X-ray detectors to constitute an embodiment of the present invention includes an X-ray scintillator (X-ray sensor) as indicated with a reference number 1 in FIG. 1. A large number of such unit X-ray detectors are assembled with their X-ray scintillator portions 1 arranged in a two-dimensional array so that their front surfaces 1a may constitute an X-ray image receiving plane as shown in FIG. 3. The front surface 1a of each X-ray scintillator 1 has an area of 0.5 mm×0.5 mm.

Referring to FIG. 1, a photodiode (photosensor) 2 is coupled to the X-ray scintillator 1, which outputs a optical signal in the form of optical pulses the number of which is proportional to the intensity of X-rays incident thereon. The optical signal outputted from the X-ray scintillator 1 is converted to corresponding electric pulse signals by the photodiode 2 and transferred to a counter 6 through a preamplifier 3, a comparator 4 and an AND gate 5. The comparator 4 is supplied with a standard voltage from a terminal A. the AND gate 5 is made open with a SET output Q of a flip-flop circuit 10, which is operated with a SET and a RESET signal externally supplied respectively though terminals T-s and T-r. The signal to set the flip-flop is supplied also to the CLEAR terminal of the counter 6. The counter 6 is thus made to start counting with the contents cleared by the same pulse as that to set the flip-flop 10, and the high-ranking four-figure value of the counter output is memorized by a register 11 as data for correcting the sensitivity of this unit X-ray detector, that is, of the scintillator 1 and the photodiode 2 (the combination of the X-ray scintillator 1 and the photodiode 2 is hereinafter termed as "scintillator/photodiode 1-2" or "scintillator/photodiode combination 1-2") The four-figure value stored in the register 11 is used to being the flip-flop 10 from a SET state to a RESET state after a period inversely proportional to the four-figure value. The signal to bring the flip-flop to a RESET state is outputted through a coincidence circuit 14 and an OR gate 13. The coincidence circuit 14, which consists of four AND gates A-1 to A-4, reads out the four-figure value and input it to the OR gate 13 from the register 11 in accordance with four timing signals supplied externally through terminals T-1 to T-4. On the other hand all of the output signals from the counter 6 are outputted to a picture signal output busline 9 through a picture signal output gate 7, which is made open by the instruction signal from an addressing circuit 8. The addressing circuit is operated by an addressing signal supplied through an address designation data busline 12. The address designation data busline 12 and the leads wires connected to the terminals A, T-s, T-r, T-1 to T-4, and K constitute a group of X-ray sensor control lines and are indicated, in FIG. 1, with a one-dot chain line 15 enclosing them.

In the above constitution of the unit X-ray detector, when the X-ray image receiving plane constituted with a two-dimensional array of the X-ray scintillators 1 belonging to many unit X-ray detectors of the same kind is first irradiated with uniform X-rays to obtain correction data for correcting the sensitivity variations among the scintillator/photodiode combinations 1-2 of the individual unit X-ray detectors, the AND gate 5 is kept open for a predetermined period of time, the period being the same for all the unit X-ray detectors and determined by the flip-flop (10) RESET and SET signals externally supplied from the terminals T-r and T-2, respectively, Since the incident uniform X-rays are thus detected by all the unit X-ray detectors for the same period of time, the number of the pulses passing through the AND gate 5 depends on the sensitivity of the scintillator/photodiode in each of the unit X-ray detector. Accordingly, the value stored in the register 11 up to the high-ranking four figures also depends on the sensitivity of the scintillator/photodiode 1-2, the level of each of four output terminals I to IV of the register 11 is made high successively in the order of I to IV in accordance with the sensitivity of the X-ray scintillator/photodiode 1-2. Therefore, in case the scintillator/photodiode 1-2 has, for example, the highest sensitivity, all the four terminals I to IV are kept at high level. On the other hand, in another extreme case where the scintillator/photodiode 1-2 is of the lowest sensitivity, only the level of the terminal I is made high. In the above process of detecting the uniform X-rays, the picture signal output gate 7 is kept closed.

Figure 4:
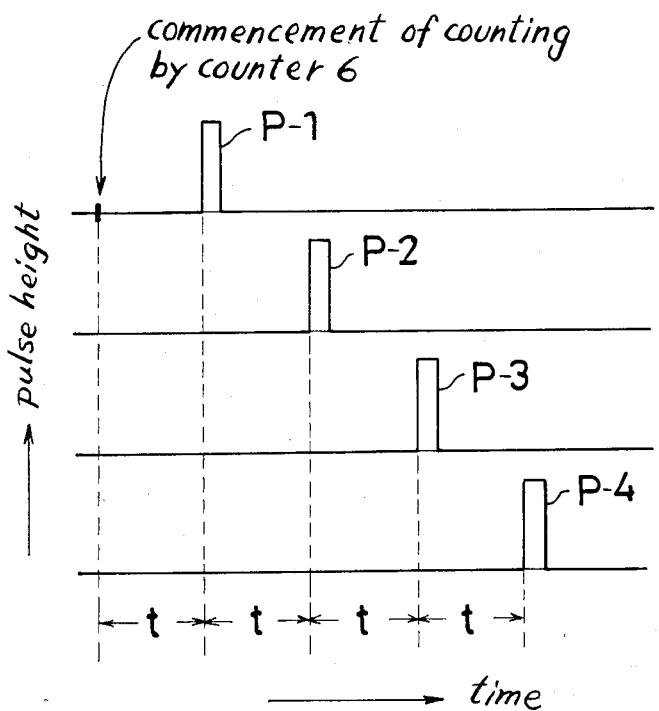
FIG. 4 shows a plot of the timing pulse intervals.

In case an X-ray image projected on the X-ray image receiving plane is detected after the above preparation, the AND gate 5 is made open again by the SET output Q from the flip-flop 10 with the register 11 kept holding the previously stored correction data. The counter 6 starts counting the pulse signals inputted thereto from the AND gate 5, while the output from the counter 6 is sent out to the picture signal output busline 9 through the picture signal output gate 7 kept now open by the instruction from the addressing circuit 8. After a predetermined time t, the above mentioned four timing pulse signals p-1, p-2, p-3 and p-4 as shown in FIG. 4 are supplied respectively to the terminals T-1, T-2, T-3 and T-4, from an external control circuit. With these pulses supplied, if the scintillator/photodiode 1-2 is of the highest sensitivity and accordingly, all the outputs at the terminals I to IV of the register 11 have been kept at high level, the AND gate A-1 of the coincidence circuit 14 first outputs a high level signal according to the pulse p-1. The high level signal is supplied to the RESET terminal of the flip-flop 10 through the OR gate 13, causing the AND gate 5 to be closed and making the counter 6 stop counting. Once the AND gate A-1 is opened to output the RESET signal to the flip-flop 10 in accordance with the pulse p-1, the following output signals from the AND gates A-2 to A-4 have no effect on the closed state of the AND gate 5. Accordingly, in case the scintillator/photodiode 1-2 is of the highest sensitivity, the X-ray given by the X-ray image is detected only for the (shortest) period t. In another extreme case where the scintillator/photodiode 1-2 is of the lowest sensitivity, a RESET signal is supplied to the flip-flop 10 for the first time when the pulse p-4 is supplied to the terminal T-4 after a period of 4t has passed since the opening of the AND gate 5, because the output level of the register 11 is kept high only at the terminal IV. In case of the lowest-sensitive scintillator/photodiode 1-2, therefore, the X-ray detection period is four times as long as that in case of the highest-sensitive scintillator/photodiode 1-2. In case of a scintillator/photodiode 1-2 having an intermediate sensitivity, as is anticipated from the above two exemplified extreme cases, the X-ray detecting period is 2t or 3t in accordance with the sensitivity of the scintillator/photodiode 1-2. In the present embodiment the sensitivity adjustment of each unit X-ray detector is made with the scintillator/photodiode sensitivy classified into four ranks. The number of sensitivity ranks can, however, be increased to five by providing one additional rank lower than the fourth. In this case the fifth timing pulse delayed from p-4 (FIG. 4) by t can be supplied to the flip-flop only through the OR gate with the coincidence circuit neglected.

Figure 2:
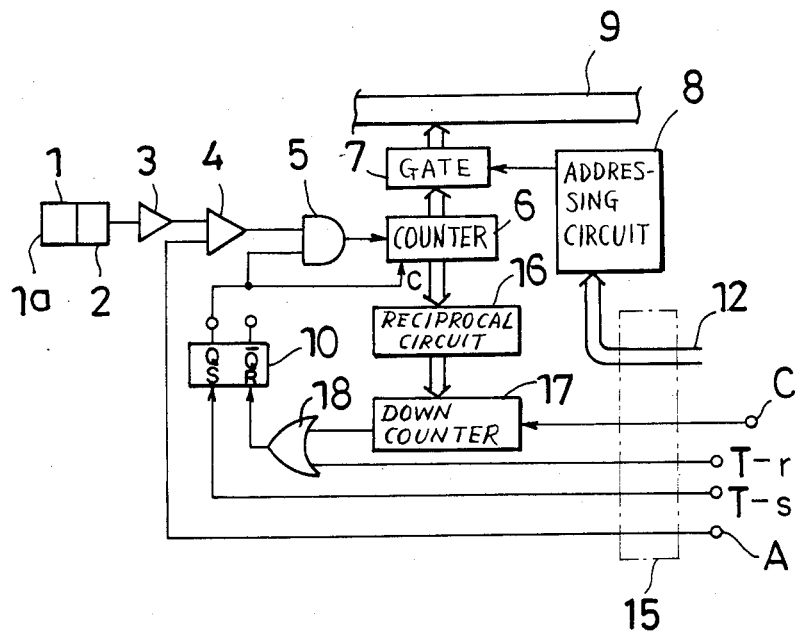
FIG. 2 shows a circuit constitution of the unit X-ray detector used in another embodiment of the present invention.

The present invention can be embodied also by constituting each of the unit X-ray detectors with a circuit as shown in FIG. 2, in which the elements corresponding to those of FIG. 1 are provided with the same reference signs as those used in FIG. 1. According to this embodiment, a reciprocal circuit 16 supplies to a down-counter 17 the reciprocal values of the count number outputted from the counter 6. The down-counter 17 is supplied also with a series of clock pulses from an external control circuit through a terminal C, and until the down-counter 17 counts down to zero, the counter 6 continues counting the input pulses. Further, this embodiment (in which each of the unit X-ray detectors is provided with the reciprocal circuit 16) can be modified by employing one common reciprocal circuit instead of providing all the unit X-ray detectors with their respective reciprocal circuit.

In the previous unit X-ray detector shown in FIG. 1, the timing pulse interval t (FIG. 4) corresponds to the exposure time of an ordinary camera, while that shown in FIG. 2 the period during which the down-counter output remains positive corresponds to the exposure. Therefore, the exposure time of each of the X-ray detectors used in the present invention can be precisely determined in accordance with the sensitivity of the scintillator/photodiode.

The unit X-ray detector applicable to the present invention can be constituted also as follows. As to the X-ray sensor (scintillator/photodiode), the X-ray image signal input circuit, the counter which is to provide a picture signal in accordance with an X-ray signal inputted thereto and the picture signal output circuit, the present X-ray detector has the same constitution as those shown in FIGS. 1 and 2, comprising the same AND gate as those 5 of FIGS. 1 and 2 in front of the counter. However, the picture brightness irregularity correcting means differently constituted with a register, a switching element for connecting the output of the counter to the input of the register only when the X-ray sensor is irradiated with uniform X-rays to obtain the picture brightness irregularity correction data, and a comparator which is to compare the output from the register with an externally supplied comparison signal whose magnitude increases inversely proportional to the time passage since the commencement of detecting an X-ray image. When the X-ray sensor (scintillator/photodiode) is irradiated with uniform X-rays for a predetermined period of time to obtain the brightness irregularity correction data, the output from the counter is memorized in the register with the above switching element put on. The counter output at this time is in proportion to the sensitivity of the X-ray sensor and may well be termed "sensor sensitivity signal". Next, while an X-ray image to be detected is projected on the X-ray sensor, the comparator compares the sensor sensitivity signal with the above comparison signal, and generates a pulse when the comparison signal increases to the value equal to the sensor sensitivity signal. This pulse makes the AND gate in front of the counter be closed through a flip-flop circuit as similarly as in the case of FIGS. 1 and 2, causing the counter to stop counting the X-ray image signal pulses outputted from the X-ray sensor. Because the comparison signal increases, as mentioned previously, in inverse proportion to the time passage since the commencement of the X-ray image detection, the duration of counting by the counter and, therefore, the picture signal outputted from the counter is inversely proportional to the sensitivity of the X-ray sensor.

In all the above described examples of unit X-ray detectors, the X-ray sensor constituted with a scintillator/photodiode combination can be replaced with an element for converting X-rays directly to an electric pulse signal.

I claim:

1. An X-ray image detecting apparatus which is constituted with an assembly of unit X-ray detectors and whose X-ray receiving plane consists of a two-dimensional array of X-ray sensors for converting irradiated X-rays to an electric pulse signal, each of which X-ray sensors constitutes each of said unit X-ray detectors together with a counter for counting the number of pulses of said electric pulse signal and means for sending out the output of said counter to an output busline, each of said unit X-ray detectors further comprising:

a gate circuit for allowing said electric pulse signal to be inputted to said counter only in a period inversely proportional to the sensitivity of said X-ray sensor ; and a gate circuit control means for outputting a pulse signal to make said gate circuit open only in said period.

2. An X-ray image detecting apparatus defined in claim 1, wherein said gate circuit control means consists of a register for registering a predetermined number of figures of the count number outputted from said counter, a coincidence circuit to which the output from said register and externally supplied timing pulses are to be inputted, and OR gate circuit to which the output from said register is inputted and a flip-flop circuit whose reset signal is the output from said OR gate circuit.

3. An X-ray image detecting apparatus defined in claim 1, wherein said gate circuit control means consists of a reciprocal circuit for generating the reciprocal values of the counter number outputted from said counter, a down-counter for counting down said reciprocal values in accordance with externally supplied clock signals, a two input OR gate circuit and a flip-flop circuit.

4. An X-ray image detecting apparatus defined in claim 1, 2 or 3, wherein each of said X-ray sensors consists of an X-ray scintillator and a photosensor coupled to said X-ray scintillator.

5. An X-ray image detecting apparatus defined in claim 1, 2 or 3, therein each of said X-ray sensors is an element for converting irradiated X-rays directly to an electric pulse signal.

* * * * *